United States Patent [19]

Bajor et al.

[11] Patent Number: 6,019,975

[45] Date of Patent: *Feb. 1, 2000

[54] ANTISEBUM AND ANTIOXIDANT COMPOSITIONS CONTAINING A LOW MOLECULAR WEIGHT FRACTION OF GUGULIPID

[75] Inventors: John Steven Bajor, Ramsey; Michael Tallman, Park Ridge, both of N.J.

[73] Assignee: Elizabeth Arden Co., Division of Conopco, Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/969,263

[22] Filed: Nov. 13, 1997

[51] Int. Cl.[7] .......................... A61K 35/78; A61K 39/385
[52] U.S. Cl. ............................................. 424/195.1
[58] Field of Search ........................................... 424/195.1

[56] References Cited

U.S. PATENT DOCUMENTS

| | | | |
|---|---|---|---|
| 4,847,069 | 7/1989 | Bissett et al. | 424/47 |
| 5,273,747 | 12/1993 | Bombardelli et al. | 424/195.1 |
| 5,690,948 | 11/1997 | McCook et al. | 424/401 |

FOREIGN PATENT DOCUMENTS

| | | |
|---|---|---|
| 313 303 | 4/1989 | European Pat. Off. . |
| 96/03033 | 2/1996 | WIPO . |
| 97/10196 | 3/1997 | WIPO . |
| 97/17060 | 5/1997 | WIPO . |
| WO 9710196 A1 | 7/1997 | WIPO . |

*Primary Examiner*—Kimberly Jordan
*Attorney, Agent, or Firm*—Rimma Mitelman

[57] ABSTRACT

A low molecular weight fraction of gugulipid as antisebum and/or antioxidant active in cosmetic skin care compositions and methods. The low molecular weight fraction is capable of delivering dual benefit to the skin: controlling or preventing sebum secretion (oily skin conditions) and protecting the skin from free radical damage.

4 Claims, No Drawings

ANTISEBUM AND ANTIOXIDANT COMPOSITIONS CONTAINING A LOW MOLECULAR WEIGHT FRACTION OF GUGULIPID

FIELD OF THE INVENTION

Methods and compositions for controlling or preventing sebum secretion from sebocytes, for controlling or preventing oily skin conditions, and also for protecting skin from free radical activity.

BACKGROUND OF THE INVENTION

Sebum is skin oil which is produced by sebocytes (cells of the sebaceous glands in the skin) and is then secreted to the skin surface. Excessive amount of sebum on the skin surface results in the condition known as "oily skin." Oily skin is associated with a shiny, undesirable appearance and a disagreeable tactile sensation. Many methods and compositions exist which attempt to control the excessive sebum secretion, but none have proved totally satisfactory.

Formation of free radicals in the skin does not appear to be related to the sebum secretion. Low levels of free radicals are formed in the skin as part of the natural metabolic pathways. The level of free radicals is increased in response to UV radiation and other environmental oxidants, e.g. pollution and cigarette smoke. Increased concentration of free radicals leads to lipid peroxidation in skin cells and cellular damage, which in turn results in a premature ageing of the skin with an accompanying loss of firmness and elasticity, wrinkles, discoloration, age spots, and dryness. Antioxidants, such as vitamin E (alpha-tocopherol), decrease the level of free radicals in the skin.

Cosmetic actives which provide more than one benefit are highly desirable, both from the manufacturer's and consumer's perspective.

Guggal is obtained from a gum/resin of the plant Commiphora mukul or Commiphora wightii. Guggal contains a complex mixture of terpenes, sterols, esters and higher alcohols. The ethyl acetate extract of the resin is an oily resinous material known as "gugulipid" or "guggal lipid." Gugulipid has been used medicinally in the treatment of obesity and elevated cholesterol levels. The medicinal activity of gugulipid is attributed to two known ketonic steroids (guggulsterones).

Bombardelli et al. (U.S. Pat. No. 5,273,747) discloses the anti-inflammatory activity of gugulipid and a guggulsterone-enriched fraction thereof and their use in the treatment of benign prostatic hypertrophy and in the treatment of acne. In this regard it is important to note that although increased sebum production may be one of the many factors that lead to the formation of acne, an anti-acne agent does not necessarily possess antisebum activity. For instance, benzoyl peroxide and salicylic acid are well-established anti-acne agents, but they do not decrease sebum output. See Cunliffe, et al., "Topical Benzoyl Peroxide Increases The Sebum Excretion Rate In Patients With Acne", British Journal of Dermatology (1983) 109, 577–579; William J. Cunliffe, "Acne", p. 256, Martin Dunitz Ltd. (1989). See also Comparative Example 3 below. Furthermore, the guggulsterone-enriched fraction described by Bombardelli was obtained with ethyl acetate and did not separate compounds by molecular weight. By contrast, in the present invention a low molecular weight fraction is employed.

Bissett et al. (U.S. Pat. Nos. 4,847,071 and 4,847,069) and Piazza et al. (U.S. Pat. No. 5,521,223) disclose photoprotective and anti-wrinkle compositions containing guggal as a natural anti-inflammatory. Although some compounds may be anti-inflammatory through antioxidant pathways, not all anti-inflammatory mechanisms are antioxidant mediated, nor are all antioxidant antiinflammatory. Put another way, antiinflammatory and antioxidant effects do not necessarily follow each other.

McCook et al., U.S. Pat. No. 5,690,948, discloses cosmetic antisebum and antioxidant compositions containing gugulipid or an alcoholic fraction thereof. McCook et al. do not teach the use of a low molecular weight fraction. Since gugulipid is dark-brown color and has a tar-like consistency at room temperature, it is difficult to work with and it is difficult to manufacture commercially attractive compositions with gugulipid. The alcoholic fraction has the same shortcomings as gugulipid and, in addition, its yield is relatively low.

It has been found, as part of the present invention, that a low molecular weight fraction of gugulipid is easier to formulate, due to its lower viscosity and better color than any one of: gugulipid, the alcoholic fraction or a high molecular weight fraction. The low molecular weight fraction can also be obtained in a higher yield than the alcoholic fraction. In chemical art, lower molecular weight does not necessarily correlate with lighter color or lower viscosity, especially when naturally occurring plant-derived compounds are surveyed. For instance, naringenin has the molecular weight of 272.2, yet it is brown, whereas glycyrrhizic acid has the molecular weight of 822.92, yet it is colorless. Likewise, tristearin (molecular weight 891.5) is a solid, whereas triolein (approximately the same molecular weight: 885.4) is a liquid.

The art discussed above does not address the need for an agent which contains both antisebum and antioxidant activities and yet is attractive in color and other physical properties and can also be obtained in high yield. Furthermore, as far as fractions of gugulipid are concerned, the above art discloses fractionation based on polarity (ethyl acetate fraction of Bombardelli or alcoholic fraction of McCook), not based on molecular weight. The use, activities and advantages of a low molecular weight fraction are not disclosed or suggested.

SUMMARY OF THE INVENTION

The present invention includes a low molecular weight fraction of gugulipid and also includes a cosmetic composition for care of the skin, the composition comprising the low molecular weight fraction of gugulipid in a cosmetically acceptable vehicle.

Another aspect of the present invention includes a method of reducing, preventing or controlling sebum secretion from sebocytes by applying to the skin a composition comprising a low molecular weight fraction of gugulipid in a cosmetically acceptable vehicle.

Still another aspect of the invention is controlling or preventing an oily skin condition, especially in the facial area, by applying to the skin a composition comprising a low molecular weight fraction of gugulipid in a cosmetically acceptable vehicle.

Yet another aspect of the invention is a method of protecting the skin from free radical activity (i.e., relieving the oxidative stress in the skin) by applying to the skin a composition comprising a low molecular weight fraction of gugulipid in a cosmetically acceptable vehicle.

Still another aspect of the invention is a method of simultaneously controlling or preventing sebum secretion while also protecting the skin from free radical damage, by the use of a single active agent: a low molecular weight fraction of gugulipid.

The inventive methods and compositions provide control of sebum secretion from sebocytes, improved oil control and improved skin feel, prevent shine and stickiness, while also protecting the skin from damaging free radical activity, which results in reduced appearance of wrinkles and aged skin, improved skin color, improved appearance of photo-aged skin, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts of material or conditions of reaction and/or use are to be understood as modified by the word "about." All amounts are by weight of the final composition, unless otherwise specified.

The term "skin" as used herein includes the skin on the face, neck, chest, back, and scalp.

The inventive methods and compositions may employ from 0.0001 to 10 wt. %, preferably from 0.001 to 3 wt. %, and most preferably from 0.01% to 2 wt. % of gugulipid or an alcoholic fraction or a low molecular weight fraction of gugulipid.

The low molecular weight fraction is obtained by dispersing or dissolving gugulipid in a polar solvent, such as alcohol (e.g., methanol) and then separating by ultrafiltration to obtain a fraction of 1,000 Da or less, preferably 800 Da or less and optimally of 500 Da or less. The solvent is then evaporated under nitrogen by e.g. gentle heat/steam bath.

Gugulipid may be obtained from the following suppliers:
C. Mukul extract: Indena (Seattle, Wash.)
Pt. Cosmetique Java, Bogar (Campo R&D, Singapore)(C. wightii extract also available).

Cosmetically Acceptable Vehicle

The compositions according to the invention also comprise a cosmetically acceptable vehicle to act as a dilutant, dispersant or carrier for gugulipid and/or the alcoholic fraction thereof in the composition, so as to facilitate its distribution when the composition is applied to the skin.

The vehicle may be aqueous, anhydrous or an emulsion. Preferably, the compositions are aqueous or an emulsion, especially water-in-oil or oil-in-water emulsion. Water when present will be in amounts which may range from 5 to 99%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants. Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Various types of active ingredients may be present in cosmetic compositions of the present invention. Actives are defined as skin benefit agents other than emollients and other than ingredients that merely improve the physical characteristics of the composition. Although not limited to this category, general examples include anti-acne agents, additional anti-sebum agents, and sunscreens.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from 0.1% to 2% by weight of the composition.

Powders may be incorporated into the cosmetic composition of the invention. These powders include chalk, talc, kaolin, starch, smectites clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor ingredients may range anywhere from 0.001% up to 20% by weight of the composition.

Use of the Composition

The composition according to the invention is intended primarily as a product for topical application to human skin, especially as an agent for controlling or preventing oily skin, for improving skin's radiance and clarity and finish, and for preventing or reducing the appearance of wrinkled, dry, aged or photoaged skin.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The topical skin composition of the invention can be in any form, e.g. formulated as a lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The composition may also be included in capsules such as those described in U.S. Pat. No. 5,063,057, incorporated by reference herein.

The following specific examples further illustrate the invention, but the invention is not limited thereto.

EXAMPLE 1

This example demonstrates the procedure for obtaining a low molecular weight fraction of gugulipid.

In the first experiment to prepare a low molecular weight fraction of gugulipid, complete gugulipid was passed through a 50,000 MW filter. The filtrate was collected and passed through a 10,000 MW filter. This was followed by filtration through 5000 MW and 500 MW filters. Analysis of each fraction by high performance thin layer chromatography revealed carryover in each fraction. In other words, compounds present in the 500 MW filtrate were seen in the other fractions. However, components present in the 50,000 MW filtrate were not seen in the lower MW filtrates. It is believed that entrapment of the smaller MW components by larger, possibly polymeric, components interfered with filtrate efficiency.

In a second experiment, complete gugulipid was filtered through a 500 MW filter only. The second experiment is described in a greater detail hereinbelow. The low molecular weight fraction obtained from the second experiment was used in the Examples below.

Materials

Gugulipid (Lot #42941-38285) standardized to 10% total guggalsterone was from Indena® (Seattle, Wash.) and HPLC grade methanol was from Fischer Scientific (Fair Lawn, N.J.). The Ultrafiltration unit was a 50 mL Amicon 8050 Ultrafiltration cell and the membrane was a YC05 500 Da cutoff filter (Cat. No. 13022), both from Millipore (Bedford, Mass.). The air tank used to supply pressure to the filtration cell was a T (tall) size nitrogen tank fitted with a Fischer Scientific FS-700 nitrogen pressure gauge.

The pressure gauge was always preset to deliver a maximum pressure of 35 psi and then increased as needed. The filtration unit itself cannot be operated safely at pressures above 75 psi.

It should be noted that a 500 Da cutoff filter may potentially have an error of +300 Da. Thus the filter employed may have passed molecules up to about 800 Da.

Filter Preparation

The YC05 filter was prepared by floating it for 30 min.(shiny side down, which is the side that will eventually face the sample) in a 1.0 L beaker containing 1.0 L of Milli-Q water. The filter was then placed in the filter support of the filtration unit (shiny side up) and the sealing rubber "O" ring put in place. The solvent holding chamber of the filtration unit was placed on top of the filter support, and then the locking plate attached to finger tightness.

The membrane was rinsed with 25 to 30 mLs of the HPLC grade methanol prior to filtering the gugulipid samples. The alcohol was added by a graduated 50 mL transfer pipette and the magnetic stir assembly placed inside the solvent holding area. The top of the filtration unit was then affixed to allow proper movement of the stir assembly, and the entire unit placed inside the metal holding bracket. The entire apparatus was then placed on a magnetic stir plate and the line from the nitrogen tank attached.

The main valve to the nitrogen tank was opened (preset to deliver 35 psi) and the magnetic stir plate was put on setting 4 ( on a setting scale of 1 [slow] through 6 [fast]). As the methanol began to flow through the membrane and out the effluent line, the pressure was slowly increased to a maximum of 55 psi so that a final flow rate of 3 to 4 mLs/min was attained. As it is not advised to run the membranes to complete dryness, the methanol rinse was terminated at a point to leave 1 to 2 mLs of solvent above the filter membrane. This was done by closing the main valve to the tank at the time the solvent had decreased to the desired point, and then venting the pressure from the filtration cell by way of its release valve.

Filtration of gugulipid

The gugulipid extract was dissolved to a final concentration of 6.5% (w/v) gugulipid using the HPLC grade methanol specified. After 10–15 min., gugulipid was dissolved in the solvent yielding a clear, medium brown solution ( similar to ice tea). Upon standing, a fine talc-like, white precipitate was observed to make a thin coating at the bottom of the container. Gentle swirling of the solution caused the precipitate to slightly opacify the solution, but this would again clear if the solution was allowed to stand unaggitated for a few minutes.

The same process used to prepare the filter was also used to filter the gugulipid. The solution was vigorously stirred during sample removal so that a representative aliquot of the solution and precipitate could be removed. A total volume of 50 mL was delivered to the solvent holding chamber by way of a graduated transfer pipette, and the unit reassembled as outlined above. The maximal pressure used to filter the gugulipid did not exceed 55 psi. Once the sample had been decreased to 1–2 mLs, the system was vented and 25 mLs of clean methanol was introduced to the solvent holding chamber. This was then passed through the filter to the same point and repeated again with 15 mls of methanol.

All effluent was collected in the same container ( approximately 90 mLs) and represented the low molecular weight fraction. The retentate material (still residing in the solvent holding chamber or on the filter itself) was collected by extensive rinsing of the filter and holding chamber with methanol. This material was then collected together and represented the high molecular weight fraction material.

The containers containing both fractions were placed on a Pierce Reacti-therm III heating module equipped with a Reacti-vap III nitrogen drying assembly. Under a constant nitrogen stream of 2 psi, the heat was slowly increased over 20 min. to a maximum setting of 4–5 ( setting range 1 [low] to 10 [high]). These conditions were maintained until the samples reached complete dryness. After allowing the containers to cool to room temperature, samples were redissolved in small amounts of methanol and quantitatively transferred to pre-tarred test tubes for mass determinations.

84% of the gugulipid was recovered in a low molecular weight fraction.

Different Characteristics of the Fractions Recovered

The physical characteristics of the high molecular weight and the low molecular weight fractions were found to be quite different. The high molecular weight fraction is more similar to the starting gugulipid material in that it still has a black tar-like color and consistency at room temperature. The low molecular weight fraction has a golden/amber color and, although it is quite viscous, it does have a certain fluid character at room temperature.

EXAMPLE 2

This example reports an in vitro analysis of sebum suppression of gugulipid and various fractions thereof.

In Vitro Sebocyte Lipogenesis Assay

Human sebaceous glands were isolated from the nose of a male (age 60) and cultured using submerged tissue culture techniques (Bajor et al, *J. Invest. Dermatol.* 102: 1994, P. 564). These sebocytes accumulate intracellular lipid droplets characteristic of mature human sebum.

Harvested and passaged sebocytes were added to each well of a 48 well tissue culture plate and incubated at 37° C. in the presence of 7.5% $CO_2$ for 10 days. On the day of experimentation, the growth medium was removed and the sebocytes washed three times with phosphate buffered saline (PBS). Fresh PBS in 0.5 ml amount was added to each well and a test agent, at various concentrations as indicated in Table 1. Quadruplicate wells were utilized for each sample. Controls consisted of PBS, dimethyl sulfoxide (DMSO) used to solubilize the lipophilic compounds, and gugulipid (which is known to both have an anti-secum activity and pass the in-vitro sebocyte assay). The cultures were incubated at 37° C./7.5% $CO_2$ for 30 minutes. Radioactive label was prepared by adding 100 µl of $^{14}C$ labelled acetic acid (Amersham, sodium salt, specific activity of 56 mCi/mmol) to 10 ml of 50 mM sodium acetate buffer. Then, 50 µl was added to each well containing the sebocytes and test agents. The cultures were returned to the incubator for four hours. Thereafter, the sebocytes were rinsed three times with fresh PBS to remove unbound active and radioactive label. Radioactive label remaining in the cultured sebocytes was counted using a Beckman scintillation counter. The results were expressed as % reduction compared to control (DMSO).

The results that were obtained are summarized in Table 1.

TABLE 1

| Treatment | Concentration | % Reduction | STD DEV |
|---|---|---|---|
| EXPERIMENT 1 | | | |
| Gugulipid | 0.01% | 50.9 | 11.7 |
| Low MW fraction | 0.01% | 47.9 | 8.6 |
| Low MW fraction | 0.04% | 54.5 | 10.5 |
| EXPERIMENT 2 | | | |
| Gugulipid | 0.01% | 62 | 6.9 |
| Low MW fraction | 0.01% | 53.6 | 7.0 |
| Low MW fraction | 0.04% | 61.4 | 4.2 |

It is evident that the low molecular weight fraction has excellent anti-sebum activity. When a high molecular weight fraction was tested, a similar reduction in sebum secretion was obtained. The use of a low molecular weight fraction is advantageous, however, in that it is easier to formulate than either the gugulipid or the high molecular weight fraction: the low molecular weight fraction is less viscous and has a gloden/amber rather than dark brown/black color. The low molecular weight fraction is further advantageous compared to the alcoholic fraction because it can be obtained in a higher yield than the alcoholic fraction.

COMPARATIVE EXAMPLE 3

The sebocyte assay described in Example 2 was repeated with various compounds as indicated in Table 2. All compounds in Table 2 are outside the scope of the invention.

The results that were obtained are summarized in Table 2. Negative values indicate increase in sebum production.

TABLE 2

| Treatment | Concentration | % Reduction | STD DEV |
|---|---|---|---|
| Estradiol | 0.0028% (100 µM) | 39.7 | 7.9 |
| Dihydrotestosterone | 0.00003% (1 µM) | −28.8 | 4.1 |
| Salicylic Acid | 0.14% (10.0 mM) | 3.6 | 7.4 |
| cis-guggalsterone | 0.10% | −46.6 | 12.4 |
| | 0.05% | 2.7 | 8.1 |
| | 0.01% | 2.7 | 8.8 |

The results in Table 2 demonstrate that the sebocyte assay is a valid and reliable test for measuring sebum suppression, because estradiol (estrogen-like compound) provided sebum suppression, as predicted from the other sources, whereas dihydrotestosterone (androgen) actually increased sebum production, as also predicted from other sources. Salicylic acid, a known anti-acne agent did not inhibit sebum output, demonstrating that an antiacne agent does not necessarily have antisebum activity. Cis-guggulsterone did not reduce sebum secretion, indicating that an active in gugulipid and in the low molecular weight fraction thereof which provides antisebum activity is not cis-guggulsterone.

EXAMPLE 4

This example reports a chemical assay and an in vitro analysis of antioxidant activity of the low molecular weight fraction of gugulipid.

Chemical Assay

Chemical assay measures the antioxidant activity of various test compounds indicated in Table 3 (each tested at a concentration of 0.08%, except the low MW fraction, which was tested at 1.67% and 0.17%). 2,2'azino-di-[3-ethylbenzthialoine sulphonate] (6.1 µmol/l) and metmyoglobin (610 µmol/l) were solubolized in phosphate buffered saline (5mmol/l, pH 7.4). Test materials were then added and absorbance was measured at 734 nm before and after addition of the substrate, hydrogen peroxide (250 µmol/l). The initial absorbance was subtracted from the substrate containing absorbance. This prevents discrepancies in absorbance due to the test compound itself. The absorbance changes with time, thus multiple time points were examined. Results were expressed as % oxidation relative to a control containing all assay components but deionized water instead of test reagent (100% oxidation). A high number means no prevention of oxidation, a poor antioxidant. The antioxidant activity of Trolox (registered trademark of Hoffman-LaRoche), a water soluble form of vitamin E was measured to establish the validilty of the test. Trolox was purchased from Aldrich (2.5 mmol/l).

The results that were obtained are summarized in Table 3.

TABLE 3

| TEST MATERIAL | % oxidation at 3 minutes relative to water control | % oxidation at 6 minutes relative to water control | % oxidation at 9 minutes relative to water control |
|---|---|---|---|
| Trolox (water soluble vitamin E) | −0.70 | 15.8 | 44.6 |
| Total Gugulipid | 2.8 | 4.4 | 5.1 |
| Ethanol | 98.79 | 91.16 | 87.5 |
| cis-guggulsterone | 100 | 97.9 | 97.4 |
| Low MW fraction (at 0.167%) | 49.70 | 44.86 | 42.59 |
| Low MW fraction (at 1.67%) | −43.83 | −28.06 | −21.37 |

It is evident from the results in Table 3 that the low molecular weight fraction has excellent anti-oxidant activity, at both concentrations tested. Cis-guggulsterone had a very inferior anti-oxidant activity, proving that it is other actives, not cis-guggulsterone, that impart anti-oxidant activity to gugulipid or to the alcoholic fraction of gugulipid. The chemical assay outlined above measures antioxidant activity obtained via direct free radical quenching, not via antiinflammatory pathway. The assay establishes that gugulipid and the low molecular fraction thereof act as antioxidants via direct free radical quenching.

EXAMPLE 5

The following is a typical antisebum and anti-oxidant composition within the scope of the present invention:

Oil Controlling Lotion

| INGREDIENT | % W/W |
|---|---|
| DI Water | QS |
| Propylene Glycol | 1.000 |
| Xanthan Gum | 0.200 |
| Disodium EDTA | 0.100 |
| Methylparaben | 0.300 |
| Polysorbate 20 | 1.500 |
| Octyl Methoxycinnamate | 2.000 |
| Low MW fraction of Gugulipid | 0.001 |
| Cetyl Alcohol | 1.500 |
| PEG-165 Glycerol Stearate | 3.000 |
| Propylparaben | 0.100 |
| Cyclomethicone | 15.000 |
| Dimethicone | 2.000 |
| Dimethiconol | 0.500 |
| Micronized Titanium Dioxide | 0.500 |
| Sodium Hyaluaronate 1% sln | 3.000 |
| Triethanolamine 99% | 0.200 |
| Salicylic Acid | 0.200 |
| Phenoxyethanol | 0.350 |

EXAMPLE 6

A leave-on facial emulsion composition is prepared by combining the following components utilizing conventional mixing techniques.

| INGREDIENT | % WEIGHT |
|---|---|
| Water | qs |
| Glycerin | 3.00 |
| Cetyl Palmitate | 3.00 |
| Cetyl Alcohol | 1.26 |
| Glyceryl Monohydroxy Stearate | 0.74 |
| Dimethicone | 0.60 |
| Stearic Acid | 0.55 |
| Octyldodecyl Myristate | 0.30 |
| Potassium Hydroxide | 0.20 |
| Carbomer 1342 | 0.125 |
| Tetrasodium EDTA | 0.125 |
| DMDM Hydantoin and Iodopropynyl | 0.10 |
| Low molecular weight fraction of Gugulipid | 0.10 |
| Carbomer 951 | 0.075 |

This emulsion is useful for providing control of sebum secretion and protecting the skin from free radical damage.

EXAMPLE 7

A leave-on facial emulsion composition is prepared by combining the following components utilizing conventional mixing techniques.

| INGREDIENT | % WEIGHT |
|---|---|
| Water | qs |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Cyclomethicone and Dimethiconol | 0.50 |
| Octyldodecyl Myristate | 0.30 |
| Potassium Hydroxide | 0.20 |
| Carbomer 1342 | 0.125 |
| Tetrasodium EDTA | 0.10 |
| DMDM Hydantoin and Iodopropynyl | 0.10 |
| Low MW fraction of gugulipid | 0.05 |
| Carbomer 951 | 0.075 |

EXAMPLE 8

The following are additional examples of typical antisebum and anti-oxidant composition within the scope of the present invention:

EXAMPLE 8A

Skin Cream (Oil in Water type)

| Chemical | % w/w |
|---|---|
| Water | qs |
| Disodium EDTA | 0.100 |
| Polysorbate 40 | 2.000 |
| Butylene Glycol | 3.000 |
| Glycerin | 5.000 |
| Methylparaben | 0.300 |
| Low molecular weight fraction of Gugulipid | 0.100 |
| Isopropyl Palmitate | 2.000 |
| Isostearyl Isostearate | 3.000 |
| Dimethicone, 200 cst | 2.000 |

-continued

| Chemical | % w/w |
| --- | --- |
| Cyclomethicone | 10.00 |
| Imidazolidinyl Urea | 0.200 |
| Polyacrylamide | 3.000 |

EXAMPLE 8B
Skin Cream (Oil in Water type)

| Chemical | % w/w |
| --- | --- |
| Water | qs |
| Carbopol 1382 | 0.300 |
| Disodium EDTA | 0.100 |
| Tween 40 | 5.000 |
| Propylene Glycol | 1.000 |
| Glycerin | 3.000 |
| Methylparaben | 0.300 |
| Triethanolamine 99% | 0.300 |
| Squalane | 1.000 |
| Low molecular weight fraction of Gugulipid | 0.500 |
| Shea Butter | 0.500 |
| Cetyl Alcohol | 1.500 |
| Octyl Palmitate | 2.000 |
| C12-15 Alkyl Benzoate | 5.000 |
| Octyl Stearate | 2.000 |
| Silicone 344 Fluid (Cyclomethicone) | 2.000 |
| Imidazolidinyl Urea | 0.200 |

EXAMPLE 8C
Skin Cream (Oil in Water type)

| Chemical | % w/w |
| --- | --- |
| Water | qs |
| Carbopol 1382 | 0.250 |
| Disodium EDTA | 0.100 |
| Butylene Glycol | 2.000 |
| Glycerin | 3.000 |
| Methylparaben | 0.250 |
| Triethanolamine 99% | 0.250 |
| Capric/Caprylic Triglyceride | 5.000 |
| Shea Butter | 0.500 |
| Cetyl Alcohol | 1.000 |
| PEG-100 Glycerol Monostearate | 4.000 |
| C12-15 Alkyl Benzoate | 6.000 |
| Tocopheryl Linoleate | 0.500 |
| Low MW fraction of Gugulipid | 0.250 |
| Silicone 200 Fluid (Dimethicone) | 2.000 |
| Imidazolidinyl Urea | 0.200 |

EXAMPLE 8D
Micro Emulsion

| Chemical | % w/w |
| --- | --- |
| PPG-5-Ceteth-20 | 4.000 |
| PEG-40 Hydrogenated Castor Oil | 1.750 |
| Polyglyceryl-10 Decaoleate | 10.00 |
| PEG-8 Caprylic/Capric Glycerides | 10.00 |
| SDA Alcohol 40B | 12.00 |
| Isodecyl Neopentanoate | 16.00 |
| Glyceryl Trioctanoate | 8.000 |

-continued

| Chemical | % w/w |
| --- | --- |
| Cyclomethicone (DC 344 Fluid) | 8.000 |
| Propylparaben | 0.100 |
| Isostearic Acid | 2.500 |
| Low MW fraction of gugulipid | 0.300 |
| Phenoxyethanol | 0.300 |
| Deionized Water | QS |

EXAMPLE 8E
Skin Cream (Water in Oil type)

| Chemical | % w/w |
| --- | --- |
| Cyclomethicone (DC 344 Fluid) | 12.000 |
| Dimethicone (DC 200/10 fluid) | 2.000 |
| Dimethicone Copolyol | 2.500 |
| Cetyl Dimethicone | 0.500 |
| C12-15 Alkyl Benzoate | 3.000 |
| Low molecular weight fraction of Gugulipid | 0.500 |
| Glycerin | 3.000 |
| Propylene Glycol | 2.000 |
| Disodium EDTA | 0.100 |
| Methylparaben | 0.250 |
| Sodium Chloride | 1.200 |
| Phenoxyethanol | 0.200 |
| Deionized Water | QS |

EXAMPLE 8F
Anhydrous Serum

| Chemical | % w/w |
| --- | --- |
| SD Alcohol 40 B (200 proof) | 20.00 |
| Cyclomethicone (DC 344 Fluid) | 2.500 |
| Squalene | 1.000 |
| Octyl Isononanoate | 2.500 |
| Dimethicone (DC 200 Fluid) | 5.200 |
| Isononyl Isononanoate | 30.00 |
| PEG-7 Glyceryl Cocoate | 1.000 |
| Polyglycerol Ricinoleate | 3.000 |
| Low molecular weight fraction of Gugulipid | 1.000 |
| Butylene Glycol | 1.000 |
| Propylparaben | 0.100 |
| Dimethiconol | 2.750 |

EXAMPLE 8G
Sunscreen Lotion (Oil in Water type)

| Chemical | % w/w |
| --- | --- |
| Water | qs |
| Disodium EDTA | 0.100 |
| Butylene Glycol | 2.000 |
| Glycerin | 5.000 |
| Methylparaben | 0.250 |
| Octyl Methoxycinnamate | 7.500 |
| Benzophenone-3 | 2.500 |
| Shea Butter | 0.500 |
| Cetyl Alcohol | 1.500 |
| Octyl Palmitate | 2.000 |
| C12-15 Alkyl Benzoate | 2.000 |

-continued

| Chemical | % w/w |
|---|---|
| Silicone 200 Fluid (Dimethicone) | 1.000 |
| Low MW fraction of Gugulipid | 2.000 |
| Imidazolidinyl Urea | 0.200 |
| Laureth-7, Polyacrylamide | 3.500 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic composition for skin care comprising
   (a) from 0.0001 wt. % to 5 wt. % of a low molecular weight fraction of gugulipid having the molecular weight below about 500 Da, as an anti-sebum agent; and
   (b) a cosmetically acceptable vehicle,
   wherein the low molecular weight fraction is obtained by dispersing or dissolving gugulipid in a polar solvent, separating by ultrafiltration to obtain the fraction and subsequently evaporating the solvent.

2. A method of reducing or preventing oily skin conditions, the method comprising applying to the skin a composition comprising
   (a) from 0.0001 wt. % to 10 wt. % of a low molecular weight fraction of gugulipid having the molecular weight below about 500 Da, as an anti-sebum agent; and
   (b) a cosmetically acceptable vehicle,
   wherein the low molecular weight fraction is obtained by dispersing or dissolving gugulipid in a polar solvent, separating by ultrafiltration to obtain the fraction and subsequently evaporating the solvent.

3. A method of reducing or preventing sebum secretion from sebocytes, the method comprising applying to the skin a composition comprising
   (a) from 0.0001 wt. % to 10 wt. % of a low molecular weight fraction of gugulipid having the molecular weight below about 500 Da, as an anti-sebum agent; and
   (b) a cosmetically acceptable vehicle,
   wherein the low molecular weight fraction is obtained by dispersing or dissolving gugulipid in a polar solvent, separating by ultrafiltration to obtain the fraction and subsequently evaporating the solvent.

4. A method of protecting skin from free radical activity, the method comprising applying to the skin a composition comprising
   (a) from 0.0001 wt. % to 10 wt. % of a low molecular weight fraction of gugulipid having the molecular weight below about 500 Da, as an anti-sebum agent; and
   (b) a cosmetically acceptable vehicle,
   wherein the low molecular weight fraction is obtained by dispersing or dissolving gugulipid in a polar solvent and then separating by ultrafiltration to obtain the fraction and subsequently evaporating the solvent.

* * * * *